United States Patent
Hashiba et al.

(10) Patent No.: US 8,376,932 B2
(45) Date of Patent: Feb. 19, 2013

(54) ENDOSCOPE ENDCAP FOR SUTURING TISSUE

(75) Inventors: Kiyoshi Hashiba, Sao Paulo (BR); Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 663 days.

(21) Appl. No.: 12/605,763

(22) Filed: Oct. 26, 2009

(65) Prior Publication Data

US 2010/0121140 A1    May 13, 2010

Related U.S. Application Data

(60) Provisional application No. 61/109,337, filed on Oct. 29, 2008.

(51) Int. Cl.
*A61B 1/00* (2006.01)
(52) U.S. Cl. ........ 600/104; 600/127; 600/129; 606/139; 606/144
(58) Field of Classification Search .................. 600/127, 600/129; 606/139–150
See application file for complete search history.

(56) References Cited

U.S. PATENT DOCUMENTS

| | | | |
|---|---|---|---|
| 5,059,201 A | 10/1991 | Asnis | |
| 5,792,153 A | 8/1998 | Swain et al. | |
| 6,358,197 B1 * | 3/2002 | Silverman et al. | 600/29 |
| 6,908,427 B2 * | 6/2005 | Fleener et al. | 600/104 |
| 6,997,931 B2 | 2/2006 | Sauer et al. | |
| 7,326,221 B2 | 2/2008 | Sakamoto | |
| 7,407,505 B2 | 8/2008 | Sauer et al. | |
| 7,431,694 B2 | 10/2008 | Stefanchik et al. | |
| 7,575,548 B2 | 8/2009 | Takemoto et al. | |
| 7,704,264 B2 | 4/2010 | Ewers et al. | |
| 7,731,727 B2 | 6/2010 | Sauer | |
| 7,736,302 B2 | 6/2010 | Matsuno | |
| 7,815,565 B2 | 10/2010 | Stefanchik et al. | |
| 7,951,158 B2 * | 5/2011 | Catanese et al. | 606/151 |

(Continued)

FOREIGN PATENT DOCUMENTS

| | | |
|---|---|---|
| EP | 1584294 A2 | 10/2005 |
| EP | 1629780 A1 | 3/2006 |

(Continued)

OTHER PUBLICATIONS

International Search Report for PCT/US09/062057 mailed Jan. 19, 2010.

(Continued)

*Primary Examiner* — Matthew J Kasztejna
(74) *Attorney, Agent, or Firm* — Brinks Hofer Gilson & Lione (57) ABSTRACT

Medical systems, devices and methods are disclosed for suturing a perforation in tissue, that may be employed endoscopically and/or laparoscopically, and that offer simple, reliable and controllable placement of suture around a perforation for complete closure thereof. One embodiment of the medical device generally includes an endcap for use with an endoscope to suture an opening in tissue using a tissue anchor. The endcap has a tubular shape defined by an annular sidewall, and the sidewall defines an interior space. A side port is further defined by the annular sidewall and is in communication with the interior space. The side port is sized to receive and locate the tissue within the interior space for suturing. A support rib is positioned within the interior space and distal to the side port. The support rib and sidewall define a piercing aperture therebetween that supports the tissue being sutured.

20 Claims, 8 Drawing Sheets

U.S. PATENT DOCUMENTS

| | | |
|---|---|---|
| 8,075,573 B2 * | 12/2011 | Gambale et al. ............... 606/145 |
| 8,142,448 B2 * | 3/2012 | Pasricha et al. ............... 606/139 |
| 2002/0116011 A1 * | 8/2002 | Chee Chung et al. ......... 606/145 |
| 2003/0139752 A1 * | 7/2003 | Pasricha et al. ............... 606/139 |
| 2003/0236535 A1 * | 12/2003 | Onuki et al. ................... 606/144 |
| 2004/0158125 A1 * | 8/2004 | Aznoian et al. ............... 600/106 |
| 2006/0025654 A1 | 2/2006 | Suzuki et al. |
| 2006/0190016 A1 | 8/2006 | Onuki et al. |
| 2006/0253144 A1 | 11/2006 | Mikkaichi et al. |
| 2006/0270906 A1 | 11/2006 | Matsuno |
| 2007/0255296 A1 | 11/2007 | Sauer |
| 2008/0086153 A1 | 4/2008 | Sakamoto et al. |
| 2008/0097152 A1 | 4/2008 | Stefanchik et al. |
| 2009/0005638 A1 | 1/2009 | Zwolinski |
| 2010/0010511 A1 | 1/2010 | Harris et al. |
| 2010/0056861 A1 | 3/2010 | Spivey |
| 2010/0211086 A1 | 8/2010 | Ewers et al. |

FOREIGN PATENT DOCUMENTS

| | | |
|---|---|---|
| WO | WO 2004/069056 A1 | 8/2004 |

OTHER PUBLICATIONS

International Written Opinion for PCT/US09/062057.

* cited by examiner

ENDOSCOPE ENDCAP FOR SUTURING TISSUE

CROSS-REFERENCE TO RELATED APPLICATIONS

This application claims the benefit of U.S. Provisional Application Ser. No. 61/109,337 filed on Oct. 29, 2008, entitled "ENDOSCOPE ENDCAP FOR SUTURING TISSUE" the entire contents of which are incorporated herein by reference.

FIELD OF THE INVENTION

The present invention relates generally to medical systems, devices and procedures for suturing tissue, and more particularly to endoscopically suturing openings in tissue.

BACKGROUND OF THE INVENTION

Openings or perforations in the walls of internal organs and vessels may be naturally occurring, or formed intentionally or unintentionally. These openings may be used to gain access to adjacent structures of the body, such techniques being commonly referred to as transluminal procedures. For example, culdoscopy was developed over 70 years ago, and involves transvaginally accessing the peritoneal cavity by forming an opening in the cul de sac. This access to the peritoneal cavity allows medical professionals to visually inspect numerous anatomical structures, as well as perform various procedures such as biopsies or other operations, such as tubal ligation. Many transluminal procedures for gaining access to various body cavities using other bodily lumens have also been developed. Natural orifices such as the mouth, nose, ear, anus or vagina may provide access to such bodily lumens and cavities. The bodily lumen(s) of the gastrointestinal tract are often endoscopically explored and can be utilized to provide access to the peritoneal cavity and other body cavities, all in a minimally invasive manner.

Compared to traditional open surgery or laparoscopic surgery, transluminal procedures are less invasive by eliminating abdominal incisions (or other exterior incisions) and incision related complications, while also reducing postoperative recovery time, reducing pain, and improving cosmetic appearance. At the same time, there remain challenges to transluminal procedures, including providing a suitable conduit to the openings and body cavities, robust medical devices that are maneuverable via the conduit and operable within the body cavity, sterility of the conduit, maintaining insufflation of the body cavity, proper closure of the opening, and prevention of infection. For example, when an opening is formed in a bodily wall of the gastrointestinal tract, such as in the stomach or intestines, spillage of the stomach contents, intestinal contents or other bodily fluids into the adjacent body cavity can occur. Travel of bacteria laden fluids outside of the gastrointestinal tract may cause unwanted and sometimes deadly infection.

In order to permanently close naturally occurring, intentionally or unintentionally formed perforations and allow the tissue to properly heal, numerous medical devices and methods have been developed employing sutures, adhesives, clips, tissue anchors and the like. One such class of devices aims to endoscopically close perforations, such as those within the gastrointestinal tract. Accordingly, various medical devices have been proposed that attach to the endoscope to facilitate perforation closure. Some of these medical devices employ suction to orient the tissue for suturing or anchor placement, while others employ tissue graspers or other devices to orient the tissue.

BRIEF SUMMARY OF THE INVENTION

The present invention provides medical devices, systems and methods for suturing a perforation in tissue, that may be used endoscopically and/or laparoscopically, and that offer simple, reliable and controllable placement of sutures around a perforation for complete closure thereof. One embodiment of a medical device, constructed in accordance with the teachings of the present invention, generally includes an endcap for use with an endoscope to suture an opening in tissue using a tissue anchor. The endcap has a tubular shape defined by an annular sidewall, and the sidewall defines an interior space. A side port is further defined by the annular sidewall and is in communication with the interior space. The side port is sized to receive and locate the tissue within the interior space for suturing. A support rib is positioned within the interior space and distal to the side port. The support rib extends laterally from a first position on the sidewall to a second position on the sidewall. The support rib and sidewall define a piercing aperture therebetween which is sized to be larger than a length of the tissue anchor, allowing the anchor to freely exit the interior space via the piercing aperture and side port.

According to more detailed aspects of the medical devices, the piercing aperture and the side port are located on the same lateral side of the endcap and preferably engage each other over a line. The support rib is preferably oriented longitudinally, and bisects a portion of the interior space that is distal to the side port. The endcap may also include an end wall, wherein the support rib preferably extends between the end wall and the first and second positions along the sidewall. In preferred constructions, a majority of the end wall is exposed to the endoscope permitting visualization through the end wall, and thus the endcap is preferably formed of an optical-grade plastic. The edge of the support rib defines a support surface, and together with a portion of the sidewall that is exposed by the side port, define an annular support surface for supporting the tissue during suturing.

One embodiment of a medical system, constructed in accordance with the teachings of the present invention, generally includes an endoscope, a needle assembly and an endcap. The endoscope has a working channel defining a longitudinal axis. The needle assembly has a needle defining a distal end and a needle lumen. A tissue anchor is slidably received within the needle lumen, and a suture is attached to the tissue anchor. The needle assembly is slidably received within the working channel of the endoscope. The endcap has an annular sidewall defining a proximal interior space, and an intermediate interior space, and a distal interior space. The proximal interior space is sized to receive a distal end of the endoscope. The side wall defines a side port in communication with the intermediate interior space and is sized to receive the tissue therein. The endcap includes a support rib bisecting the annular sidewall and the distal interior space to define an anchor ejection portion of the distal interior space. The anchor ejection portion is sized to receive the tissue anchor therein when the tissue anchor is in a lengthwise orientation.

According to more detailed aspects of the medical systems, the anchor ejection portion of the distal interior space is circumferentially aligned with the working channel of the endoscope. The anchor ejection portion of the distal interior space is in direct communication with the side port without any intervening structure therebetween. The area between the ejection portion of the distal interior space and the intermediate interior space defines a piercing aperture that is preferably sized to pass the tissue anchor therethrough in its lengthwise orientation.

Methods for suturing an opening in tissue utilizing the medical devices and systems described above is also provided in accordance with the teachings of the present invention. The endcap of the medical device is fitted to the distal end of the endoscope. The endoscope and medical device are introduced to a first site proximate the opening, and the tissue is positioned within the intermediate interior space of the endcap. The needle assembly is advanced distally through the tissue and the piercing aperture. A tissue anchor is deployed into the distal interior space, and the needle assembly is retracted proximally through the tissue. The endoscope and medical device can then be moved along the periphery of the opening while the tissue remains within the intermediate interior space, whereby the tissue anchor passes directly back through the piercing aperture and exits the side port. The needle assembly is advanced distally through the tissue at a second site proximate the opening and a second tissue anchor is deployed. The free ends of the suture are tightened to close the opening.

According to more detailed aspects of the methods, the free ends of the suture are pulled proximally to draw the tissue anchors closer together and close the opening. Preferably, the plurality of tissue anchors are connected to a single suture, and each tissue anchor is slidably attached to the suture. The method may thus further comprise the steps of positioning the plurality of tissue anchors around the opening and tensioning the ends of the suture to reduce the distance between the tissue anchors and compress the tissue around the opening to close the opening in a purse-string fashion.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

In the present application, the term "proximal" refers to a direction that is generally towards a physician during a medical procedure, while the term "distal" refers to a direction that is generally towards a target site within a patient's anatomy during a medical procedure.

Figure 1:
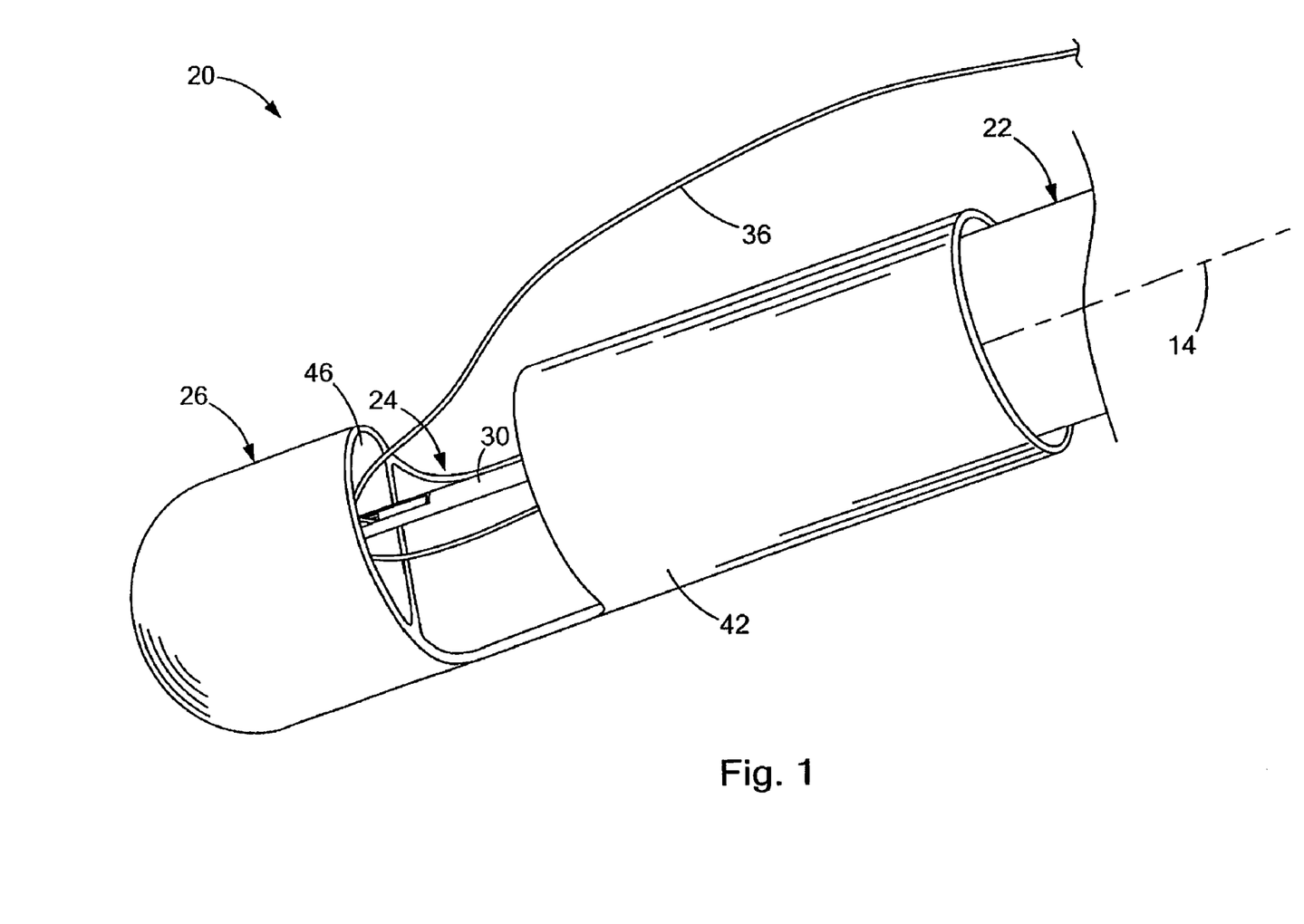
FIG. 1 is a perspective view of a medical system constructed in accordance to the teachings of the present invention.
Figure 2:
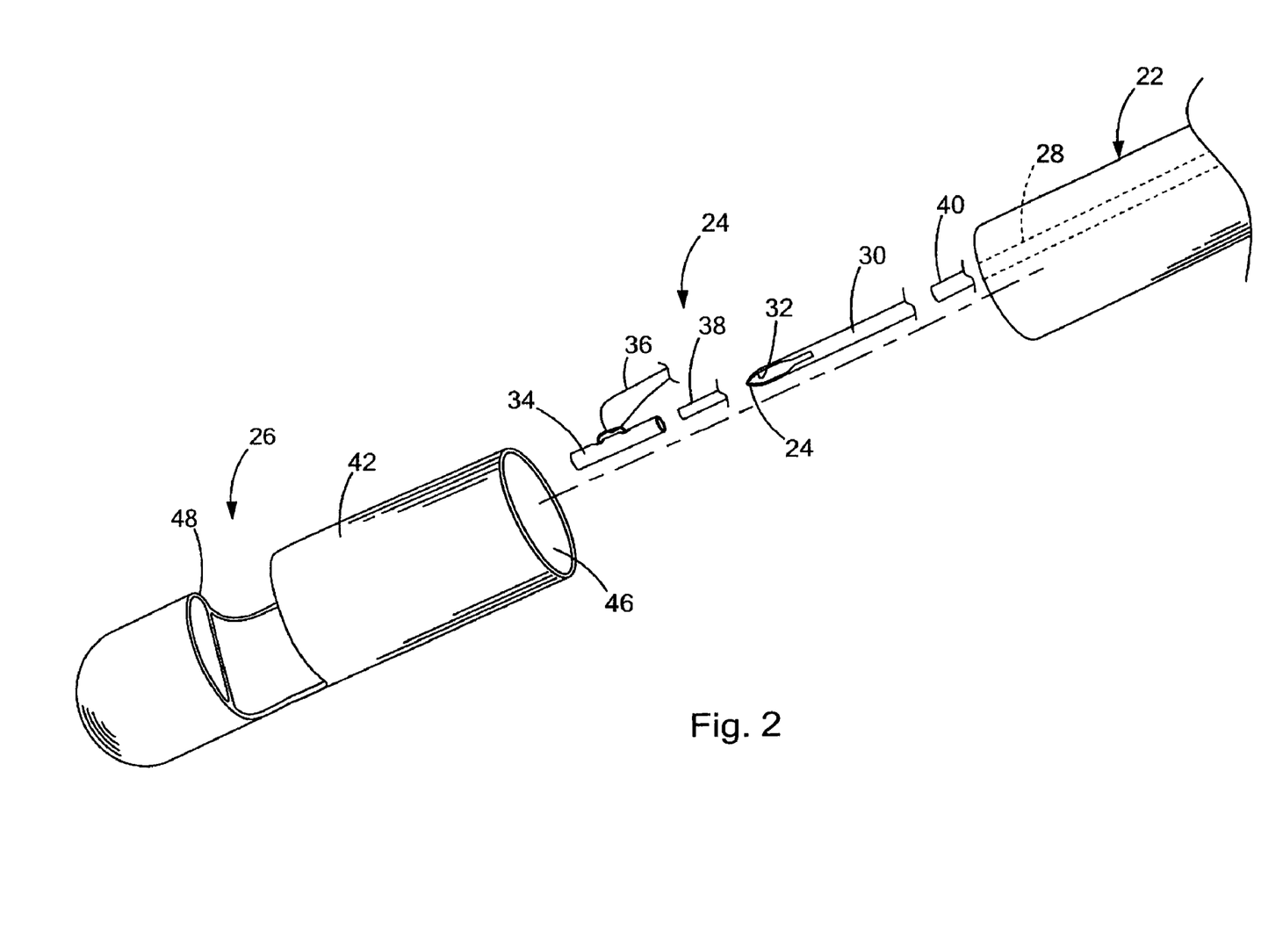
FIG. 2 is an exploded view of the medical system depicted in FIG. 1.

Turning now to the figures, FIGS. 1-2 depict a medical system 20 for suturing closed a perforation 10 in tissue 12 (see, e.g., FIG. 6), constructed in accordance with the teachings of the present invention. The medical system 20 generally comprises an endoscope 22, a needle assembly 24 and a medical device 26 adapted for use with the endoscope 22. The endoscope 22 may be any scope known to those skilled in the art, and therefore may have various lengths, diameters and functionality. The endoscope 22 generally defines a longitudinal axis 14, and a working channel 28 extends longitudinally through the endoscope 22. The needle assembly 24 is received within the working channel 28, and as best seen in FIG. 2 includes a needle 30 with a needle lumen 32 receiving one or more tissue anchors 34 having suture 36 connected thereto. A stylet 38 or other pushing element is typically fitted within the needle lumen 32 to eject the anchors 34, as is known in the art. Likewise, a needle sheath 40 may also be provided to shield and control exposure of the piercing distal tip 42 of the needle 30.

The medical device 24 generally includes an endcap 42 having a tubular or annular sidewall 44 defining an interior space 46 accessible via a side port 48 for suturing the tissue 12 with the needle assembly 24. A proximal portion 46p of the interior space 46 is sized to receive the distal end of the endoscope 22. The endcap 42 may be structured to frictionally engage the endoscope 22 for selective retention of the endcap 42 on the endoscope 22, although other means for connecting the endcap 42 to the endoscope 22 may be employed, as is known in the art. The endoscope 22 and medical device 24 are therefore adapted to be traversed through the body of a patient in this connected configuration shown in the figures.

Figure 3:
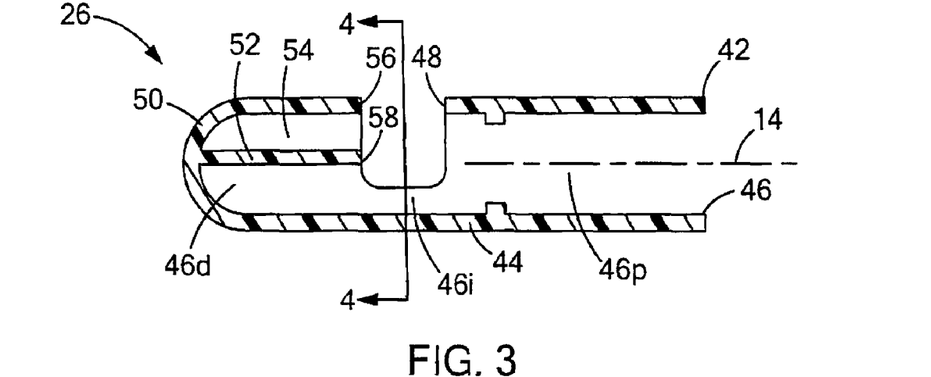
FIG. 3 is a cross-sectional view of a medical device forming a portion of the medical system depicted in FIGS. 1 and 2.
Figure 4:
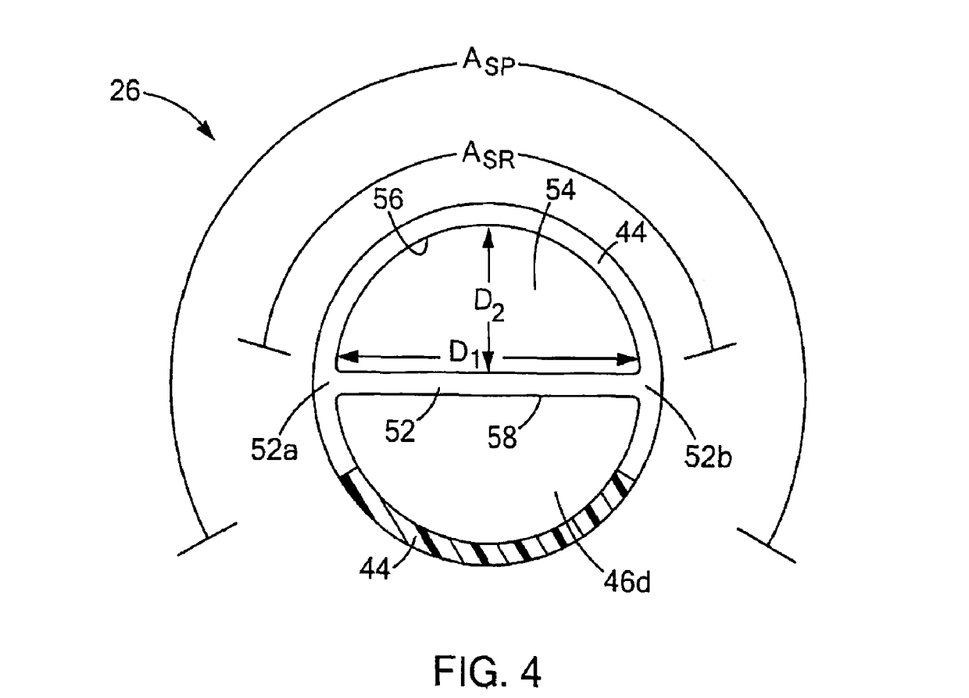
FIG. 4 is a cross-sectional view of the medical device depicted in FIG. 3.

Turning now to FIGS. 3 and 4, the medical device 26 has been shown in cross-section. The annular sidewall 44 defines an interior space 46, portions of which include the proximal interior space 46p, an intermediate interior space 46i and a distal interior space 46d. Adjacent the intermediate interior space 44i, the sidewall 42 defines the side port 46 through which the tissue 12 enters the interior space 46. The medical device 26 preferably also includes an endwall 50 located at the distal end of the sidewall 44. The endwall 50 encloses the distal interior space 46d, and is preferably constructed of an optical-grade plastic that permits the endoscope 22 to visualize through the endcap 26, discussed in greater detail herein.

The medical device 26 also includes a support rib 52 which bisects the annular sidewall 44 in the distal interior space 46d. On one side of the support rib 52, there is an anchor ejection portion 54 of the distal interior space 46d, which is defined by the space between the support rib 52 and sidewall 44. The anchor ejection portion 54 of the distal interior space 46d is sized to receive the needle assembly 24, and in particular the needle 30 and the tissue anchor 34. As best seen in FIG. 4, the support rib 52 extends from a first position 52a on the sidewall to a second position 52b on the sidewall. Thus, the support rib 52 and sidewall 44 also define a piercing aperture 56 therebetween, which is the area where the anchor ejection portion 54 meets the intermediate interior space 46i. The edge 58 of the support rib 52 defines a support surface, and together with the portion of the sidewall that is exposed by the side port 48, defines an annular support surface for supporting tissue during suturing, as will be described in further detail herein. The anchor ejection portion 54 meets the side port 48 over a line, namely the curved line of the piercing aperture 56 defined by the sidewall 44.

The piercing aperture 54 is semi-circular in shape (although it may have other shapes depending upon the tubular or annular shape of the endcap 42) defined by a largest diameter $D_1$ and a smallest diameter $D_2$. Preferably the largest diameter $D_1$ is greater than a length $L_A$ of the tissue anchor 34 (shown in FIG. 5) while the smallest diameter $D_2$ is less than the length $L_A$ of the tissue anchor 34. This helps to orient the tissue anchor 34 within the anchor ejection portion 54 of the distal interior space 46d. In another embodiment, both the largest diameter $D_1$ and the smallest diameter $D_2$ may be greater than a length $L_A$ of the tissue anchor 34. In either case, the anchor ejection portion 54 of the distal interior space 46d is sized to receive the tissue anchor 34 therein while the tissue anchor 34 is in a lengthwise orientation, meaning its axis 37 extends laterally and is generally perpendicular to the longitudinal axis 14 (i.e. within about 15 degrees of perpendicular). Likewise, the tissue anchor 34 can pass through piercing aperture 56 in its lengthwise orientation. It will be recognized by those skilled in the art that the anchor ejection portion 54 of the distal interior space 46d is in direct and immediate communication with the side port 48 without any intervening structure therebetween, permitting easy passage of the tissue anchor 34.

The sidewall 44 preferably has a circular cross-sectional shape as shown, and the first and second positions 52a, 52b on the sidewall 44 span an arc $A_{SR}$ of less than about 180 degrees, although in other embodiments $A_{SR}$ can be about 180 degrees. The side port 48 spans a second arc $A_{SP}$ which is greater than the first arc $A_{SR}$ bisected by the support rib 52. Accordingly, and as best seen in FIG. 4, the edge 58 of the support rib 52 and the exposed sidewall 44 define a support surface that has a general D-shape (see, e.g., the un-hatched area shown in FIG. 4).

As best seen in FIG. 3, the support rib 52 also extends longitudinally and engages the endwall 50. The longitudinal length of the support rib 52 positions its support surface (namely edge 58) proximate the longitudinal position of the side port 48. In the depicted embodiment, the endwall 50 has a semi-spherical shape to provide an atraumatic tip to the medical system 20, although the endwall 50 may take other shapes such as flat or conical. Notably, a majority of the endwall 50 is exposed to the endoscope 22 (see, e.g., FIG. 8) thereby permitting visualization through the endwall 50. As such, the medical device 26, and in particular endcap 42, is preferably formed of an optical-grade plastic that permits visualization therethrough. Suitable plastics include but are not limited to acrylic, polyacrylates, polyacrylonitrile, polyvinylchloride, polyetherketone, and polyethylene.

Figure 5:
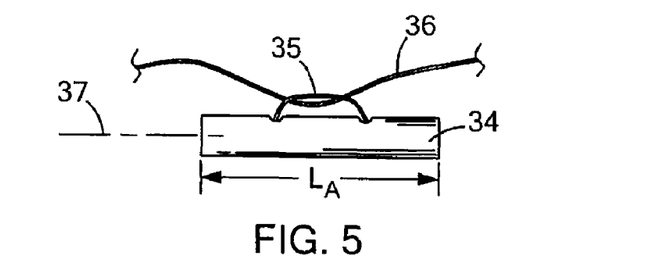
FIG. 5 is a side view of a tissue anchor forming a portion of the medical system depicted in FIGS. 1 and 2.

As shown in FIG. 5, the tissue anchor 34 is preferably of a form where the anchor member is slidable relative to the suture 36. One preferred tissue anchor 34 shown in FIG. 5, and includes a wire loop 35 which slidably receives the suture 36. Further details of this and other tissue anchors are disclosed in U.S. patent application Ser. No. 11/946,565 filed Nov. 25, 2007 and U.S. Pat. No. 5,123,914 issued Jun. 23, 1992, the entire contents of which are incorporated by reference herein.

Figure 6:
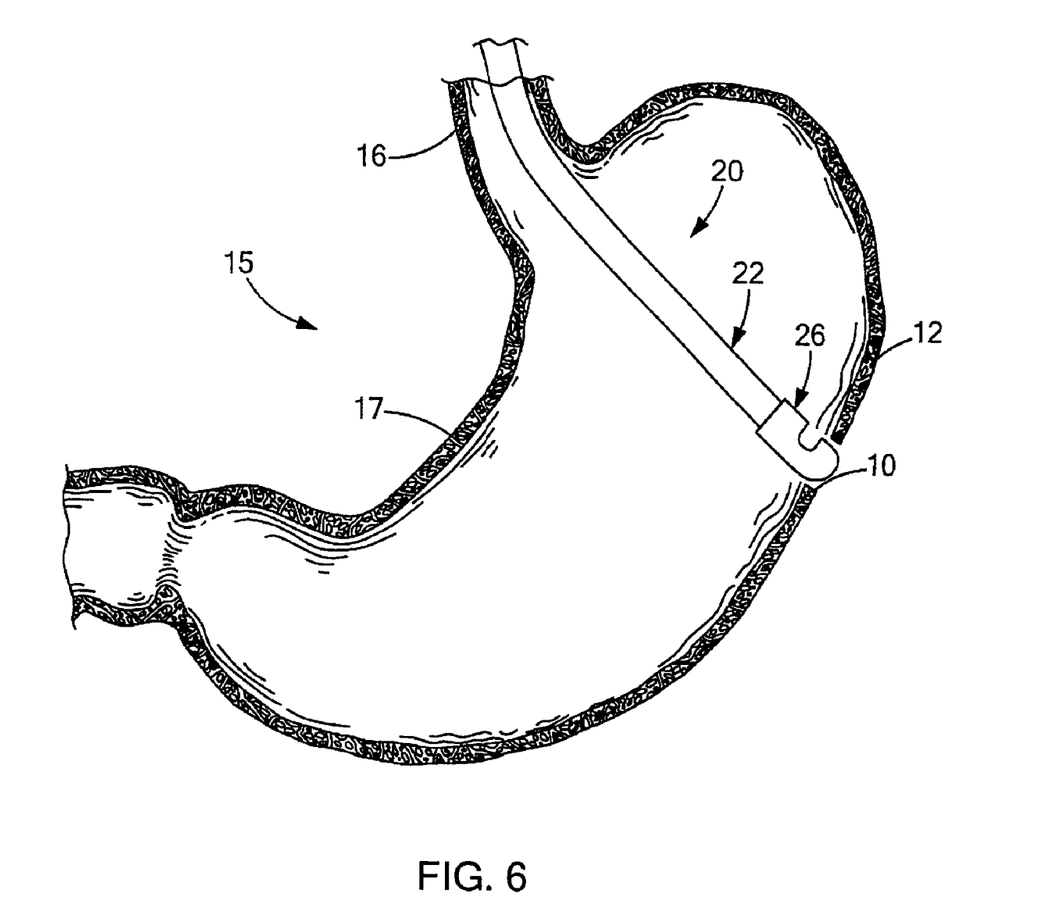
FIGS. 6-13 are views illustrating use of the medical system depicted in FIGS. 1 and 2 to close an opening in tissue in accordance with teachings of the present invention.

One preferred method for utilizing the medical system 20 and its medical device 26 will now be described with reference to FIGS. 6-13. As shown in FIG. 6, an upper portion of the gastrointestinal tract 15, such as the esophagus 16 and stomach 17, may be accessed via the mouth (not shown). A cutting instrument, with or without the aid of an endoscope or other visualization device, may be employed to form an opening 10 in the gastric wall or gastric tissue 12. Wire guides, dilators and other medical devices may be employed through the opening 10 to perform a translumenal procedure. These initial steps of the method have been described for reference purposes and to give context, and, it will be recognized that the medical system 20 of the present invention may be used to endoscopically suture any tissue within the body. Likewise, the medical system 20 may be employed through any natural orifice as (e.g., the mouth, anus, vagina, ears, nose.) as well as intentionally formed orifices such as those made during laparoscopic or similar procedures. The bodily opening 10 defined by the tissue of an internal bodily lumen may be intentionally formed or may be naturally occurring, and the internal bodily lumen may comprise a portion of the gastrointestinal tract or any other internal bodily lumen, as will be recognized by those skilled in the art.

Figure 7:
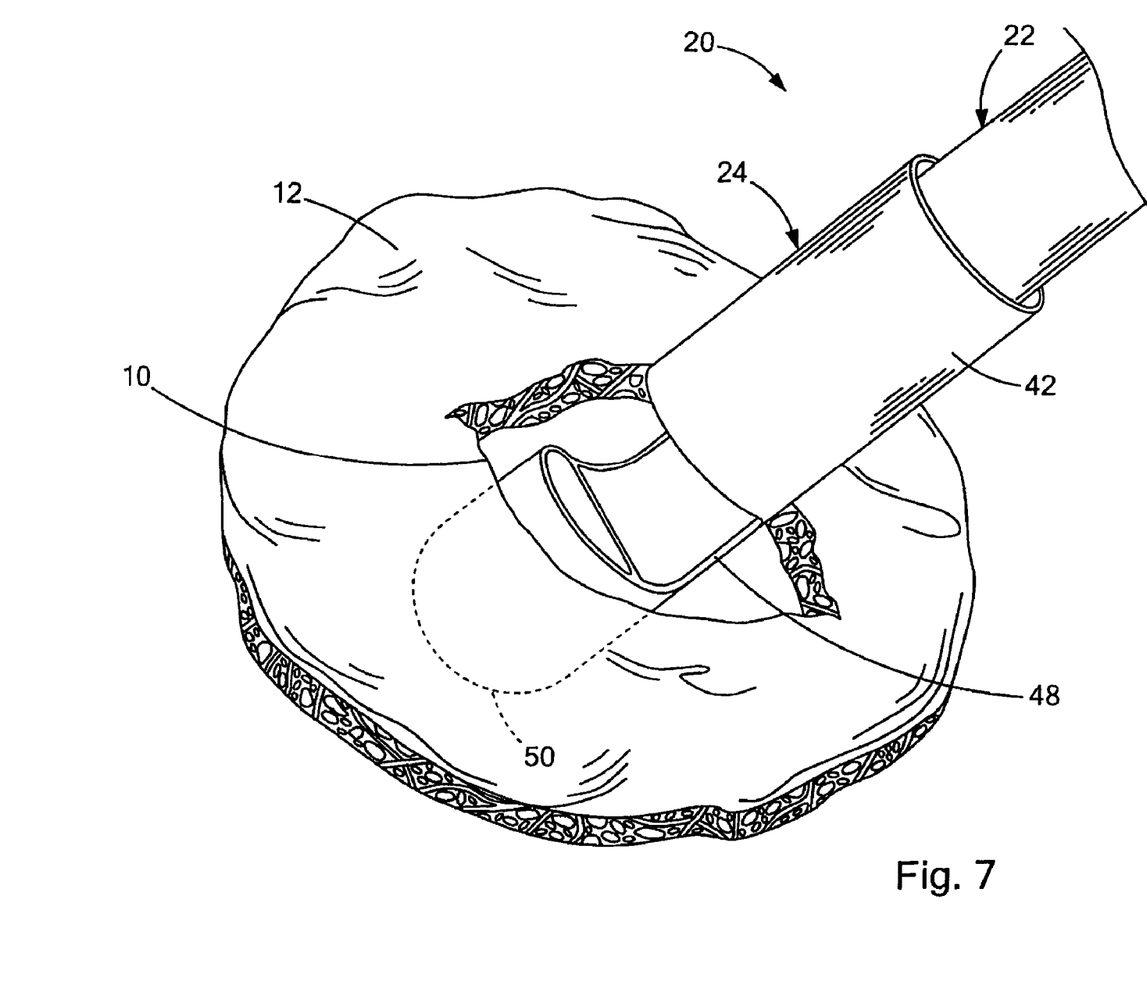
Figure 8:
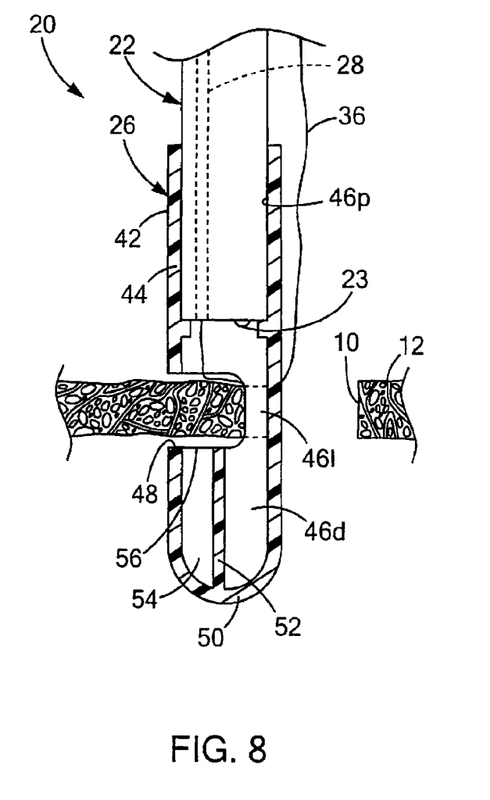
Figure 9:
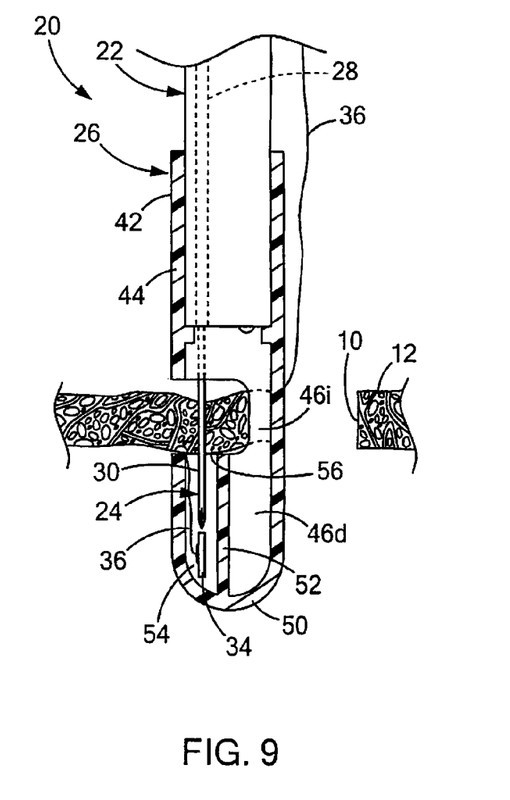

The medical device 26 and its endcap 42 are fitted on the distal end of the endoscope 22 as shown in FIGS. 1 and 6. The medical system 20 is introduced to a position proximate the opening 10, and the distal portion of the endcap 42 is passed through the opening 10 as shown in FIG. 7. As shown in FIG. 8, the medical system 20 is manipulated such that the tissue 12 passes through the side port 48 and is positioned within the interior space 46, and in particular the intermediate interior space 46i. The visualization element 23 of the endoscope 22 is capable of visualizing the placement of the tissue 12 within the interior space 46, and when there is no tissue 12 within the interior space 46, it can visualize distally beyond the medical device 26 through the endwall 50 of the endcap 42.

With the medical system 20 positioned at a first site along the tissue 12 proximate the opening 10 as shown in FIG. 8, the needle assembly 24 and its needle 30 will be advanced distally through the working channel 28 of the endoscope 22, through the tissue 12, through the piercing aperture 56 and into the anchor ejection portion 54 of the distal interior space 46d. Notably, the proximal edge 58 of the support rib 52, as well as the exposed portion of the sidewall 44, support the tissue 12 as the needle 30 is advanced therethrough. At the proximal end of the medical system 20, the stylet 38 of needle assembly 24 may be moved relative to the needle 30 to deploy the tissue anchor 34 into the anchor ejection portion 54 of the distal interior space 46d.

Figure 10:
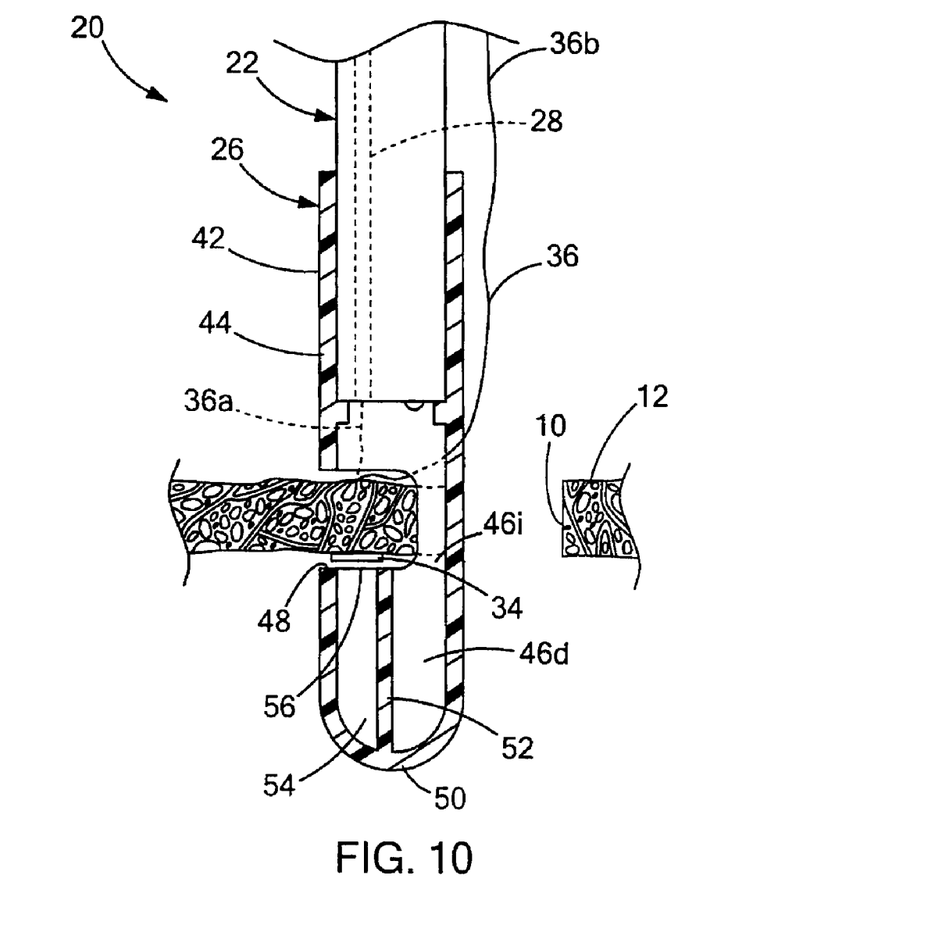

The needle assembly 24 may then be retracted proximally through the working channel 28 of the endoscope 22 such that it is removed from the tissue 12 while leaving the tissue anchor 34 on the distal side of the tissue 12, as shown in FIG. 10. The suture 36 will pass through the tissue 12, and one end of the suture will continue through the working channel 28 and/or the needle 30 for connection to additional tissue anchors 34 and to the proximal end of the medical system 20. The other free end of the suture 36 will pass through the side port 48 and along the exterior of the medical system 20 to a location outside of the body, whereby both ends of the suture 36 may be manipulated by the medical professional.

Due to the construction of the medical device 26 and its endcap 46, the tissue anchor 34 is capable of moving through the anchor ejection portion 54 of the distal interior space 46 in its lengthwise orientation shown in FIG. 10. Likewise, the piercing aperture 56 and the side port 48 permit the tissue anchor 34 to pass directly therethrough such that the medical system 20 may be slid along the periphery of the opening 10 in the tissue 12 to a second site proximate the opening 10. When the medical system is moved, the tissue anchor 34 will simply exit the medical device 26 via the side port 48 and remain at the first site where it was deployed. The medical system 20 need not be slid along the periphery of the opening 10, but may also be moved laterally away from the tissue 12 so that it exits the interior space 46, whereafter a second site may be identified and targeted for deployment of additional tissue anchors 34.

Figure 11:
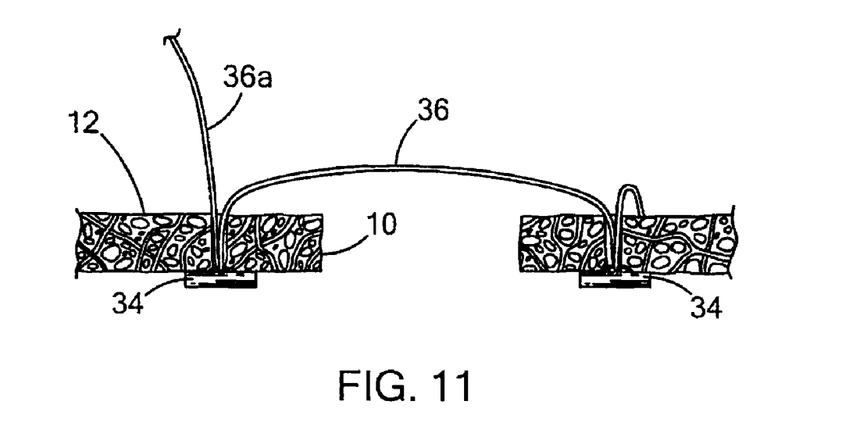
Figure 12:
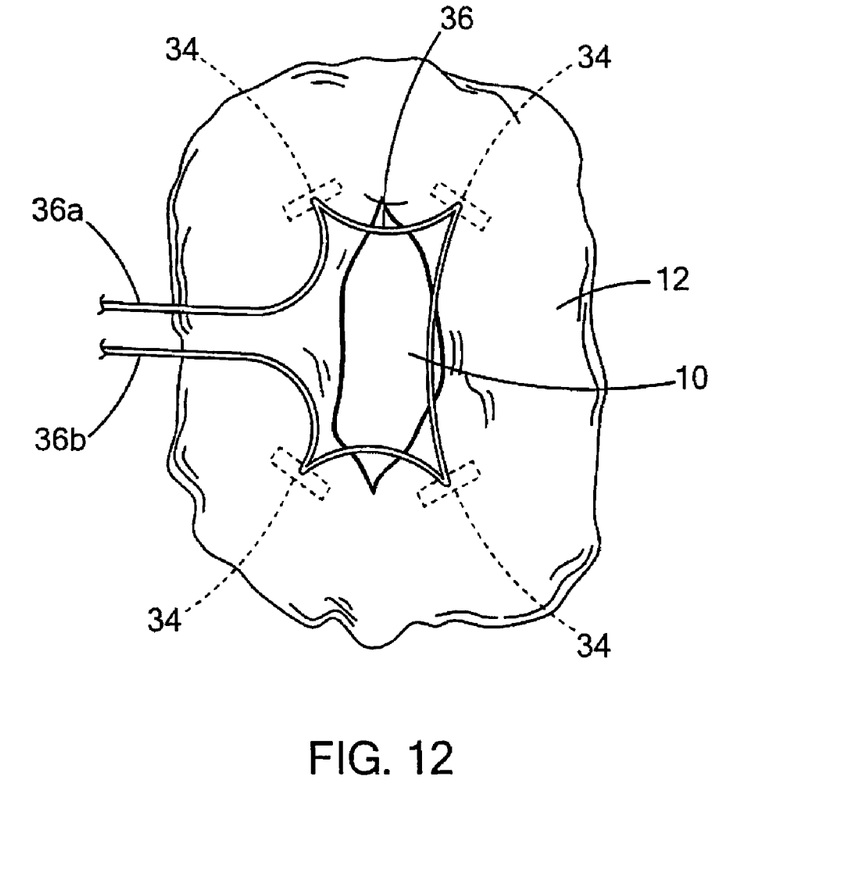
Figure 13:
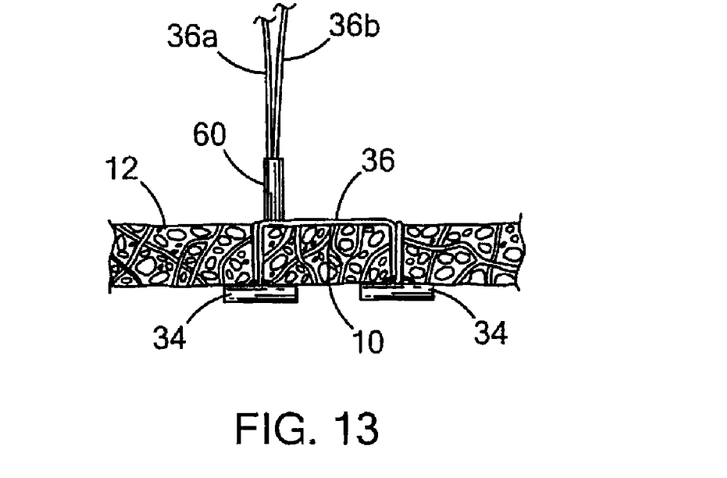

As shown in FIG. 11, multiple tissue anchors 34 may be deployed around the periphery of the opening 10 in the tissue 12, while the suture 36 largely remains on the proximal side of the tissue 12. The plurality of tissue anchors 34 may be deployed around the opening 10, such as in a generally circular configuration, although any number and any configuration of anchor deployment may be used, such as zig-zag configurations. Both of the free ends 36a, 36b of the suture 36 extend proximally through the bodily lumen and external orifice for individual manipulation by the medical professional to close the opening 10. In particular, the ends 36a, 36b may be tensioned to reduce the distance between the tissue anchors 34 and compress the tissue 12 around the opening 10 to close the opening 10 in a purse-string fashion, as shown in FIG. 13. A suture lock 60 may be employed to connect the ends 36a, 36b of the suture 36 together and maintain the tension thereon, although the suture 36 may also be tied using knots or other techniques or devices as will be readily appreciated by those skilled in the art. Several exemplary suture locks are disclosed in U.S. patent application Ser. Nos. 12/125,525 filed May 22, 2008 and 12/191,001 filed Aug. 13, 2008, the disclosures of which are incorporated herein by reference in their entirety.

It will be recognized by those skilled in the art that, while the methods described above generally include placing the tissue devices in tissue through an internal bodily lumen, it will be recognized that the systems, devices and methods may be used on any layer of material (e.g. fabrics, cloth, polymers, elastomers, plastics and rubber) that may or may not be associated with a human or animal body and a bodily lumen. For example, the systems, devices and methods can find use in laboratory and industrial settings for placing devices through one or more layers of material that may or may not find application to the human or animal body, and likewise closing holes or perforations in layers of material that are not bodily tissue.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for use with an endoscope to suture an opening in tissue using a tissue anchor, the endoscope defining a longitudinal axis, the medical device comprising:
    an endcap having a tubular shape defined by an annular sidewall, the sidewall defining an interior space, the end cap including a distal endwall;
    a side port defined by the annular sidewall, the side port in communication with the interior space, the side port sized to receive and locate the tissue within the interior space;
    a support rib positioned within the interior space and distal to the side port, the support rib extending laterally from a first position on the sidewall to a second position on the sidewall and extending longitudinally from the distal endwall, the support rib and sidewall defining a piercing aperture therebetween, the piercing aperture having a largest diameter that is greater than a length of the tissue anchor.

2. The medical device of claim 1, wherein the piercing aperture and the side port are located on the same lateral side of the endcap.

3. The medical device of claim 1, wherein the piercing aperture and the side port engage each other over a line.

4. The medical device of claim 1, wherein the support rib bisects a portion of the interior space that is distal to the side port.

5. The medical device of claim 1, wherein a majority of the distal endwall is exposed to the endoscope permitting visualization through the endwall.

6. The medical device of claim 1, wherein a proximal edge of the support rib defines a support surface.

7. The medical device of claim 1, wherein the support rib, together with a portion of the sidewall that is exposed by the side port, define an annular support surface for supporting the tissue.

8. The medical device of claim 1, wherein the sidewall has a circular cross-sectional shape, and wherein the first and second positions on the sidewall span an arc of less than about 180 degrees.

9. The medical device of claim 1, wherein the sidewall has a circular cross-sectional shape, and wherein the first and second positions on the sidewall span a first arc, and wherein the side port spans a second arc, the first arc being less than the second arc.

10. The medical device of claim 1, wherein the endcap is attached to the endoscope and the endoscope has a working channel and defines a longitudinal axis, the working channel receiving a needle assembly having a needle defining a distal end and a needle lumen, the tissue anchor slidably received within the needle lumen, and a suture attached to the tissue anchor, the support rib bisecting the annular sidewall and the interior space to define an anchor ejection portion of the interior space, the anchor ejection portion sized to receive a tissue anchor therein when the tissue anchor is in a lengthwise orientation.

11. The medical device of claim 10, wherein the anchor ejection portion of the interior space is circumferentially aligned with the working channel of the endoscope.

12. The medical device of claim 10, wherein the anchor ejection portion of the interior space is in direct communication with the side port without any intervening structure therebetween.

13. The medical device of claim 1, wherein the piercing aperture is sized to pass the tissue anchor therethrough in its lengthwise orientation.

14. The medical device of claim 1, wherein the piercing aperture has a semi-circular shape.

15. The medical device of claim 14, wherein the piercing aperture has a largest diameter and a smallest diameter, the largest diameter being greater than a length of the tissue anchor, the smallest diameter being less than a length of the tissue anchor.

16. The medical device of claim 14, wherein the piercing aperture has a largest diameter and a smallest diameter, both the largest and smallest diameters being greater than a length of the tissue anchor.

17. A medical device for use with an endoscope to suture an opening in tissue using a tissue anchor, the endoscope defining a longitudinal axis, the medical device comprising:
    an endcap having a tubular shape defined by an annular sidewall, the sidewall defining an interior space;
    a side port defined by the annular sidewall, the side port in communication with the interior space, the side port sized to receive and locate the tissue within the interior space;
    a support rib positioned within the interior space and distal to the side port, the support rib extending laterally from a first position on the sidewall to a second position on the sidewall, the support rib and sidewall defining a piercing aperture therebetween, the piercing aperture having a largest diameter that is greater than a length of the tissue anchor;
    wherein the piercing aperture has a semi-circular shape, and wherein the piercing aperture has a largest diameter and a smallest diameter, the largest diameter being greater than a length of the tissue anchor, the smallest diameter being less than a length of the tissue anchor.

18. The medical device of claim 17, wherein the endcap includes a distal endwall and the support rib extends longitudinally from the distal endwall.

19. The medical device of claim 17, wherein the support rib bisects a portion of the interior space that is distal to the side port.

20. The medical device of claim 17, wherein the piercing aperture and the side port engage each other over a line.

* * * * *